United States Patent [19]

Chvapil

[11] 4,274,410

[45] Jun. 23, 1981

[54] INTRAVAGINAL CONTRACEPTIVE AND DRUG RELEASE DEVICE AND METHOD FOR MAKING AND USING SAME

[75] Inventor: Milos Chvapil, Tucson, Ariz.

[73] Assignee: Medi-Coll, Inc., Tucson, Ariz.

[21] Appl. No.: 112,157

[22] Filed: Jan. 16, 1980

Related U.S. Application Data

[62] Division of Ser. No. 720,563, Sep. 7, 1976, abandoned.

[51] Int. Cl.³ .............................................. A61F 13/20

[52] U.S. Cl. .............................. 128/270; 128/DIG. 8

[58] Field of Search ............... 128/127, 130, 260, 261, 128/263, 270, 285, 296, DIG. 8

[56] References Cited

U.S. PATENT DOCUMENTS

| | | | |
|---|---|---|---|
| 2,610,625 | 9/1952 | Sifferd et al. | 128/296 |
| 3,094,494 | 6/1963 | Hopkins et al. | 128/285 |
| 3,157,524 | 11/1964 | Artandi | 128/296 |
| 3,639,561 | 2/1972 | Gordon et al. | 128/270 |
| 3,780,730 | 12/1973 | Weisman | 128/127 |
| 4,040,417 | 8/1977 | Zipper | 128/130 |

*Primary Examiner*—Robert W. Michell

*Assistant Examiner*—C. F. Rosenbaum

*Attorney, Agent, or Firm*—Cahill, Sutton & Thomas

[57] ABSTRACT

A contraceptive device and method of contraception as well as a method of making the contraceptive device are described. Native collagen form of fibrillar protein is comminuted and homogenized in an acid environment; noncollagenous material is removed and residual collagen is mixed with water the pH of the resulting slurry is adjusted to 4.5 to 5.0 by the addition of acetic acid; gluteraldehyde is then added and the slurry poured into molds and frozen at approximately −10° centigrade for approximately 20 hours. The frozen mass is then thawed, washed, and immersed in a wash of pH 8 to 9 for approximately 2 hours at 20° centigrade. Sufficient reducing agent is added to the wash to create excess reducing equivalents. The sponge is then immersed in a buffer solution of pH 4 to 5 for a time sufficient to equilibrate to uniform pH. The sponge formed by the above method is then moistened and self-administered in the upper vault of the vagina proximal to the cervix. The sponge is then retained for a desired period, usually several days to one month.

12 Claims, 11 Drawing Figures

INTRAVAGINAL CONTRACEPTIVE AND DRUG RELEASE DEVICE AND METHOD FOR MAKING AND USING SAME

This is a division, of application, Ser. No. 720,563,filed Sept. 7, 1976 now abandoned.

Of the great variety of contraceptive techniques presently utilized, or previously utilized and no longer advocated, all have definite undesirable aspects. Surgical techniques are confronted with unavoidable irreversibility; oral/chemical techniques have been shown to include certain undesirable side effects. Interuterine contraceptive devices have not been altogether satisfactory and, while such devices may be effective in preventing conception, there exists evidence of some local as well as systemic difficulties in a certain proportion of users; further, inconvenience attending the use of interuterine devices, such as the requirement for trained medical personnel for application, militates against their use.

Both intrauterine devices and oral contraceptives have recently been subject to criticism, suggesting heretofore unrealized or unrecognized risks to the user. With regard to some interuterine devices, recent studies pertaining to the biology of trace elements may suggest that the presence of copper in interuterine devices is a potential source of metal ions effective in catalyzing lipid peroxidation. With regard to oral contraceptive systems, it has been shown that they decrease serum zinc content and often increase copper content in the serum. Zinc is known to contribute to the integrity of biomembranes of cells and reactivity of tissues; further, zinc supplementation has been shown to inhibit platelet aggregation, the release of serotonin and also to limit the necrotic changes in the heart after isoproterenol. Decreased zinc content in the plasma following the ingestion of certain oral contraceptives may be the causal factor labelizing platelets increasing their aggregability and adhesiveness and thus be a contributing factor to the known enhanced coagulability and thereby probably contribute a higher incidence of thromboembolism in users of hormonal contraceptive drugs.

Another, and much older contraceptive technique is the utilization of an intravaginal material. Basically, intravaginal contraception techniques may be divided into three general approaches used or suggested by the prior art; first, chemical techniques (e.g. jells, foams, and the like, incorporating spermicidal agents and/or astringents); second, occlusives such as diaphragms or cervical caps; and third, tampon devices. These techniques, as used today, could be considered safer to the user than in previous ages; they are, however, inefficient and inconvenient. The present invention relates to the third category of intravaginal techniques but offers safety, efficiency and convenience.

The utilization of intravaginal tampons to prevent conception would appear to be at least over two thousand years old. Certain types of tampons constructed from plant derivatives apparently were utilized as a means of introducing spermacidal chemicals in Egypt as early as 1550 B.C. Throughout succeeding centuries substances such as cotton or wool were used as intravaginal contraceptive devices; during the Middle Ages there seems to have been some use of vegetable pulps as tampon material. There is some suggestion that during the period corresponding to the Middle Ages oriental cultures used a form of bamboo paper as an intravaginal contraception device. In more recent times, approximately the Sixteenth Century, there appears to be some evidence of the use of a sea sponge as an intravaginal contraceptive device while in the Eighteenth and Nineteenth Centuries sponges were sometimes moistened with dilute lemon juice or brandy as a spermicidal agent. More recently, rubber and natural sponges have been used and moistened with such alleged spermacidal agents as olive oil. Present day attempts to use intravaginal sponge devices sometimes incorporate a more sophisticated agent such as currently available foams.

Presently, the use of a sponge in combination with a spermacidal foam has been characterized as an inexpensive but relatively ineffectual contraceptive technique. Such prior art sponge contraceptive technique requires the insertion of the sponge into the vagina immediately before intercourse where it will remain effective for only a matter of hours; the sponge must remain in place for a period of several hours, usually six, following the last act of coitus. Any attempt to permit the sponge to remain longer is accompanied by physiologically unacceptable effects. The intravaginal contraception system of the present invention emphasizes the long term use of an intravaginal contraceptive sponge having unique properties permitting such extended use without adverse reactions.

Prior art attempts to provide a successful intravaginal contraceptive device and method through the use of various materials have generally failed to meet the requirements of efficient and convenient intravaginal contraception. A variety of sponges and sponge-like structures have been suggested, including those constructed of polyethelene foam, silico-organic rubber, neoprene, and a variety of polymers; however, in each instance, the disadvantages have prevented significant use.

There are several disadvantages with prior art attempts to prevent conception through the utilization of intravaginal tampon devices. For the device to be effective, it must dependably prevent sperm from reaching the cervical uterine canal. It is known that due to a pH of from 4 to 5 in the vagina, under normal physiological conditions, the motility and viability of spermatozoa in the vagina is limited to a relatively short time period of approximately 1 to 2 hours; in contrast, motility and viability of the spermatazoa is preserved for up to 48 hours in the uterine tract. It is therefore incumbent upon any intravaginal contraceptive method and device to totally prevent the passage of spermatozoa and maintain such blockage for at least the lifetime of the most optimistic sperm. To provide a mechanical blockage, it is therefore important for any device to form an intimate contact with the walls of the vagina while covering the cervix and to maintain the contact regardless of the expansion, contraction, change in cross-sectional configuration or other movement of the vagina and the walls thereof.

The resilience of the device must therefore provide intimate contact with the walls of the vagina while providing sufficient force against the walls to prevent dislodgement. The material must be highly absorbent both as to the volume of liquid which it will absorb and the rate at which the liquid is absorbed. Prior art devices including sponges of various compositions do not provide sufficient resiliency, are difficult to maintain in place, and exhibit low rates of liquid absorption and low total liquid capacity. Further, the material should expand while in the moist environment of the vagina to a predetermined size and shape to exert only light pressure while maintaining adherence to the vaginal mucosa. The material must be sufficiently soft to prevent interference with normal sexual intercourse and must be non-irritating both to the user and her sexual partner. The last requirement, if not satisfied, may result in itching, discharge, or dyspareunia. Further, the material should be capable of being applied without professional assistance and should be capable of remaining in place for an extended period of at least several days.

If the intravaginal contraceptive device is formed of a sponge and remains in place as mentioned above, it is imperative that the device not interfere with vaginal homeostasis with respect to pH, bacterial flora or cytology and must, of course, not contribute to or cause the generation of odor. Prior art intravaginal contraceptive devices fail to meet the above requirements and have either been abandoned as an ineffective contraceptive technique or have been used with less than total success.

If the intravaginal contraceptive device is to remain in place for at least several days, and perhaps for a period of one month, it is important that the material be stable as to its physical and biological properties during intravaginal application. However, if the device is also to be disposable, then it becomes important that the device be biodegradable in a waste disposal environment. Biodegradability of cellulose containing materials is established but their use intravaginally for an extended period of time is generally unacceptable. Rubber and polymer compounds may be stable during the period of intravaginal application but present disposal problems as a result of their incompatability with the requirements of biodegradability.

It is therefore an object of the present invention to provide an intravaginal contraceptive device that, when placed in the upper vault of the vagina proximal to the cervix, will present a mechanical barrier to the passage of spermatozoa.

It is another object of the present invention to provide an intravaginal contraceptive device that is resilient and will expand in a moist environment of the vagina to a pre-formed size and shape.

It is also an object of the present invention to provide an intravaginal contraceptive device that, when placed in the vaginal proximal to the cervix, will expand and exert light pressure on the walls of the vagina and adhere to the vaginal mucosa.

It is another object of the present invention to provide an intravaginal contraceptive device that is highly absorbent and will rapidly absorb liquid, including ejaculate.

It is still another object of the present invention to provide an intravaginal contraceptive that may be placed in the vagina proximal to the cervix without professional assistance while nevertheless remaining in place without regard to the activity of the user.

It is yet another object of the present invention to provide an intravaginal contraceptive device that, when placed in the vagina, will not interfere with vaginal homeostasis with respect to pH, bacterial flora or cytology.

It is yet another object of the present invention to provide an intravaginal contraceptive device that, when placed in the vagina, will not be irritating and will not contribute to itching, discharge or dyspareunia.

It is yet another object of the present invention to provide an intravaginal contraceptive device which, when placed in the vagina for a period of several days, will not contribute to the generation of odor.

It is yet another object of the present invention to provide an intravaginal contraceptive device, the physical and biological properties of which remain stable during an extended intravaginal application but nevertheless becomes biodegradable when placed in a waste disposal environment.

It is another object of the present invention to provide an intravaginal contraceptive device incorporating a spermicidal agent which is made available over a period of time greater than that possible with prior art devices.

It is still another object of the present invention to provide an intravaginal contraceptive device comprising a collagenous sponge material incorporating a drug that is delivered to the vaginal region during application of the device over a greater period of time than that possible with prior art devices to thereby prolong the pharmacological action of the drugs.

It is another object of the present invention to provide a method of making an intravaginal contraceptive device.

It is another object of the present invention to provide a method of making an intravaginal contraceptive device comprising collagen sponge reconstituted in molds resembling the formal anatomy of the upper vault of the vagina proximal to the cervix.

It is still another object of the present invention to provide a method of making an intravaginal contraceptive device comprising collagen sponge reconstituted to provide a resilient structure incorporating a pH approximating the natural pH of the vagina.

It is another object of the present invention to provide a safe, convenient and effective method for preventing conception.

It is still another object of the present invention to provide a method for preventing conception by blocking the passage of spermatozoa from the vagina to the uterine canal while subjecting the sperm to an environment hostile to their existence but nevertheless normal to the vagina.

These and other objects of the present invention will become apparent to those skilled in the art as the description thereof proceeds.

The present invention may be described by reference to the accompanying drawings in which.

The reconstitution of collagen may be accomplished using various techniques. The production of such collagen materials, and particularly sponges, incorporates a known process where collagen source material such as bovine skin is comminuted, suspended in water, and frozen, and the water removed by lyophilisation. Recently, an improved collagen product and method for the reconstitution of collagen has been described, i.e. U.S. Pat. No. 3,823,212. In the latter patent, collagen protein material from a suitable source such as bovine skin is mechanically comminuted, formed into an homogenous slurry in an acid environment, a tanning agent is added to the slurry and the slurry foamed. Subsequently, the slurry is poured into trays and then frozen to a predetermined temperature and incubated for a predetermined time. The resulting reconstituted collagen product is then available simply by thawing the frozen slurry and mechanically removing excess water; importantly, lyophilisation is not necessary. The specific structure obtained by the above process can be controlled to maximize or minimize physical characteristics such as resiliency and the like. The control of the product is achieved through the control of incubation time, incubation temperature and tanning agent content.

The system of the present invention contemplates an improvement in the process of the above-identified patent in the production of a new device, and the new use of the device for inhibiting contraception. In accordance with the present invention, a collagen sponge is formed from prepared native collagen derived from various animal tissues rich in the collagen form of fibrillar protein. The most convenient and common source of such collagen is bovine skin or Achilles tendons. The tissue is mechanically comminuted and homogenized in an acid environment. By repetitive extraction procedures and by specific enzyme digestion techniques, the noncollagenous material is removed without denaturing the collagenous protein material. The residual collagen, mostly in fibrillar form, is then mixed with distilled water and the pH of the resulting slurry is adjusted to between 3.5 and 6.5 and preferably to between pH 4.5 and 5.0 through the addition of acetic acid.

A tanning agent such as glutaraldehyde is then added to the slurry to crosslink the collagen; after mechanically mixing the suspension, the slurry is poured into molds of suitable size and shape, for example, resembling the formal anatomy of the vaginal fornix with the cervix.

Figure 1:
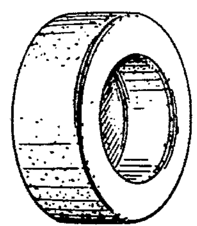
FIG. 1 is a perspective view of a collagen sponge contraceptive device constructed in accordance with the teachings of the present invention.
Figure 2:
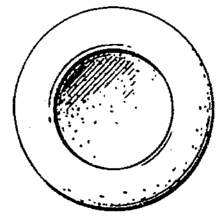
FIG. 2 is a front elevational view of the device of FIG. 1.
Figure 3:
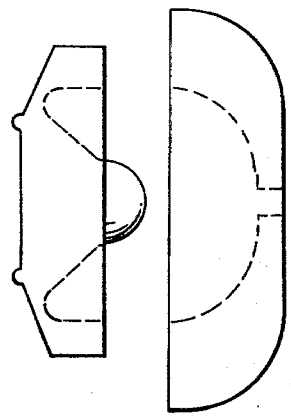
FIG. 3 is a side elevational view of a mold for receiving collagen slurry for the formation of a collagen sponge contraceptive device.
Figure 4:
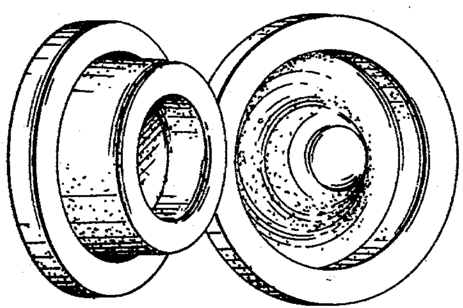
FIG. 4 is a perspective view of the mold of FIG. 3.
Figure 5:
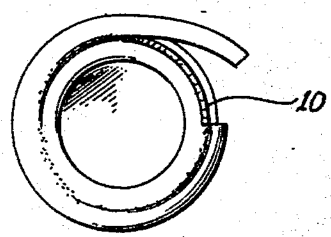
FIG. 5 is a front elevational view of another embodiment of the collagen sponge contraceptive device constructed in accordance with the teachings of the present invention.
Figure 6:
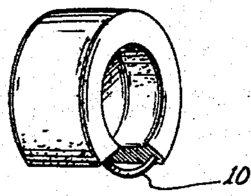
FIG. 6 is a perspective view, partly broken away, of the device of FIG. 5.
Figure 7:
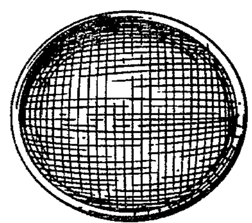
FIG. 7 is an illustration of a mesh structure of incorporation in another embodiment of the collagen sponge contraceptive device of the present invention.
Figure 8:
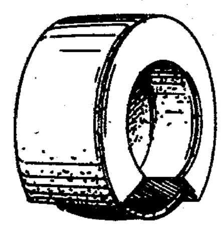
FIG. 8 is a perspective view, partly broken away, of another embodiment of the present invention incorporating the mesh of FIG. 7.

The device of the present invention may be formed as shown in FIGS. 1 and 2, having a 6 cm diameter and a 2.5 cm depth, with a central excavation 3 cm wide and 1.5 cm deep. The sizes, of course, may be changed to provide a range of sizes to accommodate expected vaginal canal sizes. The particular shape of the device is not critical and the device may alternatively be formed through the use of a mold such as shown in FIGS. 3 and 4 to provide a shape more closely comporting with the upper vault of the vagina at the fornix with a central cavity more closely conforming to the shape of a typical cervix. Further modifications may be made in the specific shape and structure of the device. For example, FIGS. 5 and 6 disclose a device having a diameter and cavity size and shape corresponding to the device of FIGS. 1 and 2; however, additional radial force may be derived from the structure of FIGS. 5 and 6 through the inclusion of a stiffening member or ring 10 formed of rubber or stainless steel. The embodiment shown in FIGS. 5 and 6 inherently incorporates a radial stiffness which is believed unnecessary except in specific circumstances. Similarly, stiffness may be added to the device structure through the utilization of a nylon fiber mesh screen as shown in the embodiment of FIGS. 7 and 8. The nylon fiber mesh also permits the sponge to more readily maintain a predetermined shape and continuously exert sufficient pressure on the vaginal wall to retain its position proximal the cervix. Under certain circumstances, it may be desirable to add to the stiffness or "spring rate" of the device through the addition of elements such as the stiffening member 10 of FIGS. 5 and 6 of the mesh of FIGS. 7 and 8; further, it may also be desirable to assist the maintenance of a predetermined shape through the incorporation of the mesh of FIGS. 7 and 8. However, the method of the present invention produces a collagen sponge having such mechanical properties that such additional elements are usually not necessary.

The suspension is reconstituted into collagen sponge by freezing the slurry at approximately −10° centigrade and incubating the frozen slurry for approximately 20 hours. The frozen mass is then thawed and the bulk of the water is removed by mechanical squeezing of the resulting collagen sponge. Collagen sponge is thus crosslinked by mono or biofunctional aldehydes (for example glutaraldehyde) and reconstituted by the described freezing procedure into the sponge. Glutaraldehyde reacts with E-amino groups of collagenous lysine or hydroxylysine amino acids under the formation of Schiff bases.

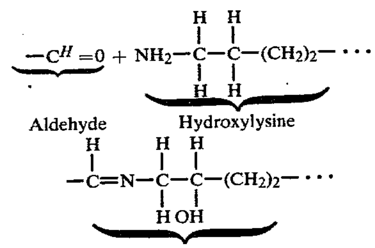

SCHIFF BASE CROSSLINK

Schiff base is known to be unstable in acid environment. Thus equilibration of the sponge with an acetate buffer to an acid pH, to be described later, may result in continuously breaking of Schiff bases; as a result, the sponge will lose its resilience (which depends on the number of crosslinks) and eventually its desirable physical characteristics. To prevent such decomposition of this form of crosslink Schiff base, it must be reduced, by any reducing agent, optimally by sodium borohydride ($NaBH_4$) alkali medium of pH 8 to 9.

By this reaction, the double bond in Schiff base is reduced to a single, very stable bond, resistant to acid treatment.

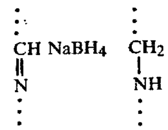

Accordingly, reconstituted and glutaraldehyde-crosslinked sponge, when thawed, is washed 5 times in tap water to remove any free aldehyde; then the pH of the wash is adjusted by sodium hydroxide to pH 8 to 9. Sufficient sodium borohydride is then added to the wash to create excess reducing equivalents. The sponge is then incubated at 20° C. for 2 hours in the wash. The washed sponge is then soaked for 30 minutes to 2 hours (sufficient time to equilibrate to uniform pH) in a buffer solution of pH 4 to 5; for example, a 0.1 to 0.5 M acetate buffer, pH 4.1. The solution is mechanically removed and the sponge dried in the air.

Any buffer system operating efficiently within the range of pH 4.0 to 5.0 could be used in order to maintain the relative concentration of hydrogen ions in the vagina environment stable. This means that an efficient buffer has a certain strength to neutralize the effect of liquids (cervical mucus, ejacuate) having slightly alkali pH. Thus, acetate or citrate buffers may be used of molar strength ranging from 0.1 to 1 M solutions to equilibrate and preserve the pH of the collagen sponge in a range of 4.0 to 7.0 and preferably to 5.0 to 6.0.

The sponge may then be immersed in a surfactant such as a solution of approximately 0.1% Triton X-100 (a commercial name for octyl phenoxy polyethoxyethanol).

There are two significant advantages accompanying the application of biologically inert surfactants to the sponge. First, the surfactant increases the rate of wetting of dry sponge by any fluid, ejaculate included. Thus, by such a treatment the rate of flux of sperm into the sponge will be increased. Second, surfactants, specifically Triton-X-100 are known spermicidal agents, used in commercially available vaginal spermicidal preparations. Alternatively, the surfactant may be added to the buffering solution and supplied to the collagen sponge concurrently with the equilibriated buffer.

The mechanical strength of the collagen sponge may be enhanced by the addition of cellulose fiber to the collagen material. When cellulose is to be added, a fibrillar cellulose material such as viscose may be added to the slurry; preferably, the material is in the form of fibers of approximately 0.5 to 2 cm in length and approximately 50u to 150u, preferably 100u in diameter. An amount of cellulose, in fibrillar form, equal to approximately 5% to 15%, and preferably 10% of the dry weight of collagen, is added to the slurry prior to reconstitution of the collagen. The resulting sponge exhibits substantially the same characteristics as the collagen sponges without the cellulose fiber addition but is somewhat mechanically stronger and more resistant to physical damage such as tearing.

Although the reconstitution of collagen by the freezing procedure will produce structures from felt-like consistency to soft sponges; there exists an optimum combination of parameters insuring the production of the desired sponge for contraceptive purposes. These parameters have been found to be as follows: the temperature of freezing should be within 0° to −20° centigrade, preferably about −5° centigrade, time of incubation of frozen slurry should be from 12 hours to 3 days, preferably about 20 hours, the amount of tanning agent, such as glutaraldehyde, should be 0.5–1% based on the total volume of the slurry.

EXAMPLE 1

A 100 ml collagen slurry was formed having a collagen content of 1% (dry weight basis). The mixture was homogenized by mechanically mixing to form a collagen slurry foam while 0.5 ml gluraldehyde was added. The foamed collagen was poured into molds, each having a 6 cm diameter and a 2.5 cm depth with a central excavation 3 cm wide and 1.5 cm deep. The collagen thus placed in the molds was then frozen at −5° C. for 20 hours. The frozen slurry was allowed to thaw at room temperature; water was then mechanically removed from the foamed collagen sponge by squeezing the thawed structures. The sponge thus formed was then washed five times in tap water and then immersed in a 500 ml tap water wash adjusted to pH 8 by the addition of sodium hydroxide. Two grams of sodium borohydride were then added to the wash to ensure an excess of reducing medium; the sponges were then incubated at 20° C. for 2 hours in the wash. The sponges were then removed, washed in tap water, and then immersed in an 0.4 M acetate buffer solution for a period of one hour. The sponge was then removed, and the excess solution mechanically removed by squeezing; the sponges were then allowed to dry in air.

EXAMPLE 2

The procedure described in Example 1 was repeated except that viscose fibers were added to the homogenized collegen mixture. The viscose fibers had an average length of 1.5 cm and an average diameter of 100u. The amount of fiber added equaled approximately 10% of the dry weight of collagen (0.1 grams).

EXAMPLE 3

The procedure described in Example 1 was repeated and the resulting sponges were then immersed in an 0.1% solution of Triton X-100. These sponges were then removed and excess solution was mechanically squeezed therefrom; the sponges were then all allowed to dry at room temperature.

An intravaginal contraceptive sponge formed by the above method exhibits a pore size varying between 80u and 1400u with an average size of 400u. The pH of an extract of the sponge will range between pH 4.0 to 7.0 and preferably between pH 4.5 to 6.0. The density of the sponge will range from 30 to 45 mg/cm$^3$. The sponge matrix incorporates a continuity of channels which, in combination with the above pore size, produces an unexpectedly high capillary pressure (or suction), thus yielding a very high rate of liquid binding as may be seen by reference to the following Table 1:

TABLE 1

Liquid Binding by Various Sponges

| Type of Sponge | Total Binding g $H_2O$/g | Rate of Binding g $H_2O$/g/15 sec. in % of total binding |
|---|---|---|
| Collagen sponge - partially crosslinked | 23 | 55 |
| Collagen sponge - maximum crosslinked | 45 | 78 |
| Polyvinylalcohol | 19 | 10 |
| Polyurethane | 31 | 12 |
| Teflon | 0 | 0 |
| Cellulose | 9 | 38 |
| Cotton | 8 | 42 |

With reference to the above table, it may be seen that the collagen sponge produced in accordance with the method described above exhibits a unique capacity for liquid binding as well as an extremely high rate of binding. Further, in the other materials listed in the table, it may be seen that a high total binding is not accompanied by a high rate binding. The polyvinylalcohol, polyurethane and Teflon materials are commercially available sponge materials; the cellulose and cotton materials are those used in commercial hygenic vaginal tampons.

Figure 9:
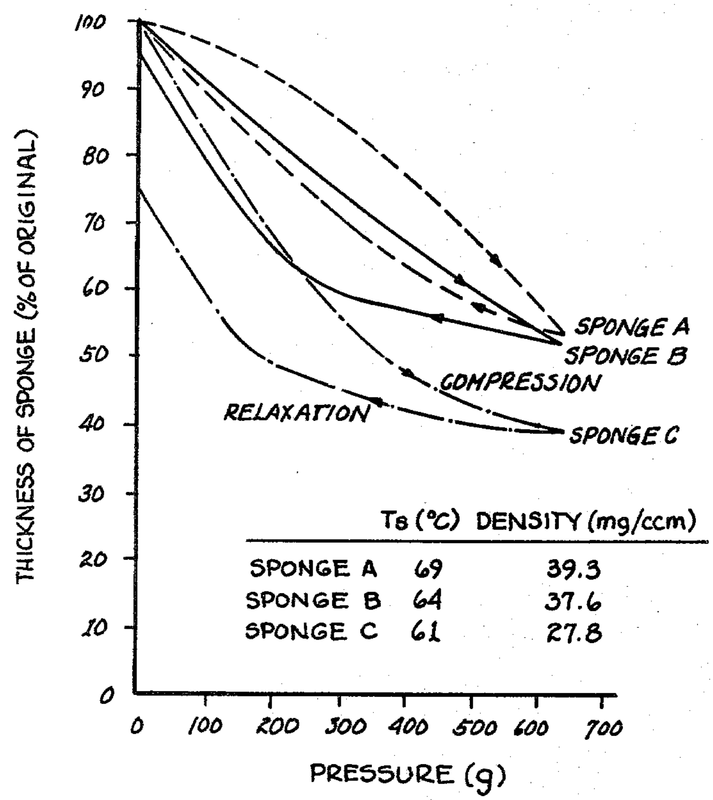
FIG. 9 is an illustration of the compression and relaxation characteristics of various collagen sponges.
Figure 10:
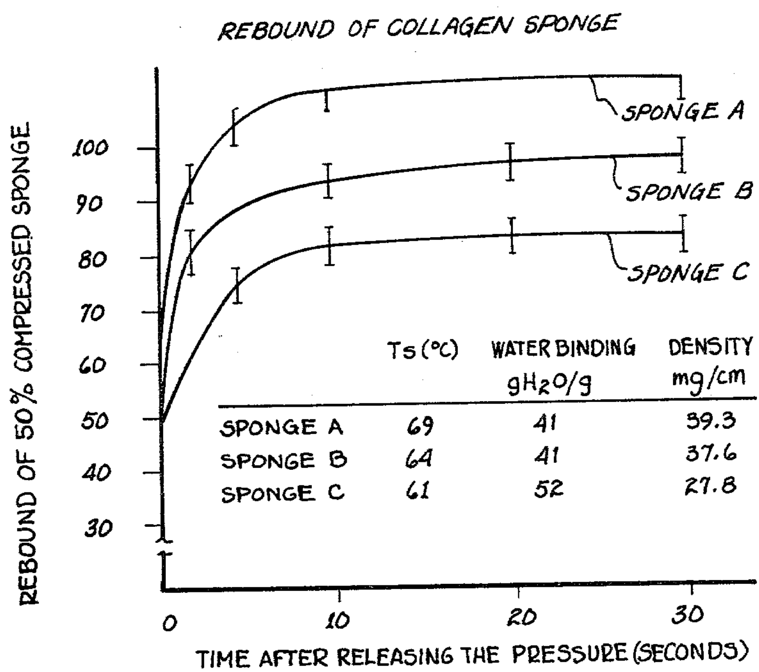
FIG. 10 is an illustration of the rebound characteristics of various collagen sponges.
Figure 11:
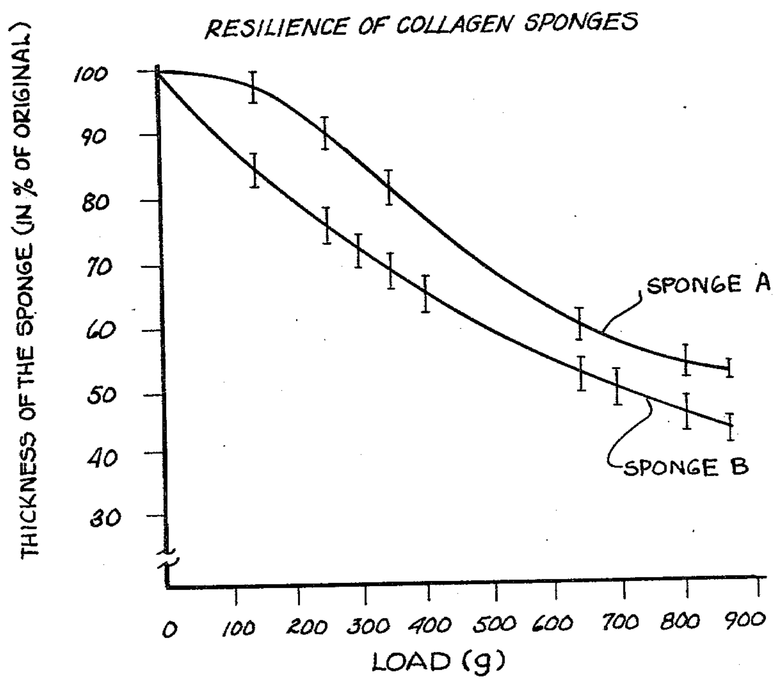
FIG. 11 is an illustration of the resilience of various collagen sponges.

As stated previously, various characteristics of the sponge of the present invention are controlled by varying certain parameters, within the stated ranges, in the reconstitution of the collagenous mass. The relationships of resiliency, rebound and relaxation characteristics with crosslinking are shown in FIGS. 9, 10, and 11. Three collagen sponges were prepared, each differing in the degree of crosslinking; the variation in crosslinking was achieved by altering the glutaraldehyde content in the foamed slurry prior to reconstitution. Each of the sponges was rated as a function of the crosslinking (degree of tanning) by determining the shrinkage temperature of the collagen. It is well known that the crosslinking in collagenous material is destroyed by subjecting the wetted collagen to elevated temperatures. The destruction of such crosslinking is initially evidenced by a marked shrinkage of the sponge; a requirement of a higher temperature to cause initial shrinking indicates a higher degree of crosslinking. Accordingly, the three sponges represented in FIGS. 9, 10, and 11 as sponges A, B, and C were rated in accordance with the degree of crosslinking present in the respective sponges by ascertaining the shrinkage temperature $T_s$ measured in degrees Centigrade.

Table II illustrates the relationship between degree of crosslinking (as determined by $T_s$) and the rate and magnitude of liquid binding capacity of the collagen sponge. In fact, collagen sponge without crosslinking collapses when placed in contact with water and serves better as a homeostatic agent than as an absorbent medium.

TABLE II

Effect Of Crosslinking Of Collagen Sponge On The Rate And Magnitude Of Liquid Binding Capacity

| Degree of Cross-Linking $T_s$ (°C.) | Liquid Binding g $H_2O$/g Dry Sponge | Rate of Liquid Binding g $H_2O$/g/10 Sec. |
|---|---|---|
| 48 | 12 | 4 |
| 56 | 27 | 15 |
| 62 | 37 | 30 |
| 69 | 45 | 45 |

The device prepared in accordance with the above method exhibits a felt-like consistency in the dry state. The dry sponge is immersed in water prior to insertion in the vaginal canal and may readily be compressed to approximately 10% of its original size in its moist condition; this reduced size renders the application of the device simple, thereby permitting self-administration without the aid of any applicator. It will be obvious, however, that the sponge may be inserted in the vagina through the use of an applicator similar to that presently used for various types of hygenic vaginal tampons. Upon deposition within the vaginal canal proximal to the cervix, the moistened sponge promptly expands to its original size and shape as shown in FIGS. 3 and 4. In this state, the sponge will make intimate contact with the vaginal mucosa and exert a very gentle pressure toward the wall of the fornix; the folding vaginal walls in the vicinity of the fornix will contribute to the force keeping the sponge in place.

The resiliency of the collagen sponge, produced in accordance with the above method, has been found to be sufficient to exert enough pressure on the vaginal mucosa to maintain its position even during expansion and contraction of the muscular walls of the vagina. The intimate contact with the vaginal mucosa by the resilient collagen sponge, prepared as set forth above, accommodates changes in vaginal dimensions during intercourse while maintaining sufficient frictional force to overcome mechanical forces that may otherwise attempt to dislodge the device, such as pressure fluctuations that may occur in the vaginal tract during intercourse.

As set forth above in connection with Table I, the collagen sponge, as prepared by the described procedure, exhibits a significantly higher total liquid binding capacity (2–6 times larger than other tested materials) than other sponge materials. A dry collagen sponge contraceptive cup having the above typical dimensions will exhibit an average weight of 2 grams with an average liquid binding capacity of 30 ml-45 ml of water per gram; therefore, the total liquid binding capacity of the device will normally be from 60–90 ml of water. The average volume of ejaculate is approximately 3–5 ml, which, when contacted by the collagen sponge, and particularly in view of the capillary pressure creating the high rate of liquid binding capacity, promptly absorbs the ejaculate and traps the seminal fluid in the surface layer of the sponge.

The sperm is thus effectively trapped within the framework of the the collagen sponge and is confronted with an extremely long passageway in any attempted progression through the sponge. As stated previously, motility and viability of spermatozoa in the vaginal environment is generally limited to no more than two hours. The device of the present invention presents an environment to spermatozoa substantially similar to the normal vaginal environment. The pH of the sponge, unlike prior art devices, effectively duplicates the vaginal environment, thus limiting the life of spermatozoa coming in contact therewith. Immobilization of spermatozoa in less than 120 seconds has been observed when subject to an environment of 4.0 pH. Table III illustrates observed motility of human spermatozoa in collagen sponge of various pH.

TABLE III

Effect Of pH Of Collagen Sponge On The Motility Of Human Spermatozoa

| pH | Time When Motility Ceased (In Minutes) |
|---|---|
| 4.0 | 1.8 |
| 5.0 | 3.7 |
| 6.0 | 12.4 |
| 7.0 | >30 |

This natural spermicidal environment, present in the vaginal canal, is enhanced in the preferred sponge by providing a pH similar to that extant in the vaginal mucosa. The naturally spermicidal vaginal mucosa and the duplication in the collagen sponge of the naturally occurring acidity (or perhaps even increasing the acidity) provides spermacidal activity in a manner compatible to, and coincident with, normal vaginal functions. The mechanical interruption of sperm migration coupled with the acid environment presented by the device of the present invention results in prompt absorption of the ejaculate into the surface of the device and almost instantaneous immobilization of spermatozoa.

In addition to the spermacidal effect of acid pH of the vagina (and collagen sponge) the low pH is an essential local preventative against microbial and fungus infections in this organ. Accordingly, acidity of collagen sponge contributes to the antibacterial and antifungus natural environment of the vagina.

Inorganic zinc or zinc in prostatic fluid or seminal plasma has been shown to immobilize spermatozoa, to inhibit their respiration and metabolism of lipids. Correspondingly, the release of zinc from human spermatozoa as induced by various chelating agents (cystein, EDTA, histidine) is accompanied by a striking increase in oxygen consumption and in mobility of spermatozoa. Although the effect of zinc on various functions of spermatozoa is not completely understood, the available literature indicates a primary inhibitory effect on cell functions. It is worth mentioning, that a similar effect of zinc has been proposed for granulocytes, macrophages, platelets, and most cells.

Collagen in the body serves as an ion exchanger binding electrolytes, metabolites, and drugs. The in vivo binding of colloidal gold and other metals to collagen are other examples of the exchange capacity of this protein. Because of the large volume of dicarboxylic and diaminoacid and residues in the collagen molecule, this protein interacts in vitrol with various substances to form complexes of varying chemical stability.

Various binding sites on the collagen molecule permit several types of metal binding. Zinc (as well as copper) containing $d^{10}$ electrons should form stable covalent bonds, although weaker ionic bonds could be formed also. In addition, simply physical retention of zinc in the fibrillar meshwork of the porous collagen sponge will render this form of free zinc readily available for a pharmacological effect on spermatozoa.

In view of the unique properties of the contraceptive sponge produced in accordance with the above method and particularly in view of the physical properties relating to the ability of the device to be utilized to prolong the pharmacological action of included drugs, the contraceptive device can be rendered additionally spermacidal through a modification of the process in its manufacture. Accordingly, to the previously described acidified collagen slurry containing glutaraldehyde, zinc chloride solution is added to obtain 100-500 uM final concentration and the method described above is followed to reconstitute the collagenous protein in contraceptive sponge form. The retention of the zinc compound through molecular binding as well as physical entrapment in the interstices of the sponge presents a unique spermacidal releasing structure.

Alternatively, the formed contraceptive collagen sponge may be immersed in a 100 to 500 uM zinc acetate solution for approximately 30 minutes. The sponge is removed from the solution and the excess solution mechanically removed. This latter addition of spermacidal compound to the collagenous sponge provides spermacidal action over a period considerably prolonged relative to the utilization of the same spermacidal solution in a non-collagen sponge. The physical and mechanical properties of the collagen sponge of the present invention provide a more intimate capture of the solution and a more regulated release of the compound during use.

One of the major problems in gynecology are virus infections of the vagina and adjacent tissues by herpes simplex virus. It has been shown, however, that multiplication of rhinovinus, which consists basically of simple ribonucleic acid molecule, is inhibited by zinc. Zinc is known to link to RNA or DNA molecules thus preventing virus division. Thus, combination of collagen sponge with $Zn^{++}$ as proposed above will not only increase spermicidal-contraceptive efficacy of collagen sponge but will also have pharmacological-therapeutic effect in situations of herpetic infections.

The unique physical properties of the contraceptive collagen sponge prepared in accordance with the above method as well as the molecular binding capacity of the device provides an unusual drug delivery system. In the treatment of bacterially related disease involving the vaginal canal, the contraceptive sponge of the present invention may be utilized to incorporate bactericidal compounds for prolonged administration to the affected areas. The bactericidal agent may be incorporated into the collagenous structure through the addition of a bactericidal solution into the aforementioned slurry prior to reconstitution of the collagen material. The drug delivery system thus made available provides an unusual means for continuously administering and prolonging the pharmacological action of the bactericide. The unique physical properties of the collagen sponge including the liquid binding capacity of the sponge, as well as the structural characteristics of the sponge, provide an excellent means for absorption of bactericidal solutions prior to application of the device to the vaginal canal. The unusual retention characteristic of the sponge again prolongs the pharmacological action of the bactericidal drug captured in the interstices of the sponge. The intravaginal contraceptive sponge of the present invention may therefore serve the role of continuous protection against Neisseria gonorrhea, treponema pallidum (syphilis), and other sexually transmitted micro-organisms when used for the administration of anti-venereal disease prophylactic drugs. For example, additions to the collagen sponge such as ortho-iodobenzoic acid, 0.1% napharsen, 1% sodium lauryl sulfate would provide the user with continuity of the protective effect, convenience, and long exposure of microorganisms to the drug, without interference with the sexual act. At the same time it was shown that the above additions to the present collagen sponge are spermicidal, thus increasing the contraceptive role of the collagen sponge.

The collagen sponge prepared in accordance with the teachings of the present invention has been found to retain its unusual properties throughout its period of use in intravaginal applications. The material does not exhibit any degradation during storage or use; however, the collagen sponge does exhibit biodegradability when placed in a waste disposal environment. While no quantified measurements were taken concerning the biodegradability of the collagen sponge contraceptive device of the present invention, the biodegradability was demonstrated by immersing samples of the devices in a typical sewage effluent. The temperature was maintained at 20° C. for one group under test and at 37° C. for another. The sponges were immersed in the effluent and were removed at predetermined times to evaluate cohesion. No quantititative measurements could be taken; however, observations were made concerning the degradiation of the sponges through their respective loss of inherent cohesion. The following Table IV illustrates those observations. A zero ("0") in the table indicates that no visible change occurred in the structure of the sponge when observed by the unaided eye and manually removed from the effluent and agitated. Each positive sign ("+") indicates an arbitrarily chosen degree of disintegration resulting from loss of cohesion of the corresponding sponge; entry in the table of four successive plus signs indicates that the sponge became totally disintegrated, suggesting a breakdown in the fibrillar structure of the sponge and digestion of the protein.

TABLE IV

| DEGRADATION OF CSC IN SEWAGE SYSTEM DEGREE OF DIGEST IN DAYS | | | | | | |
|---|---|---|---|---|---|---|
| | 7 | 14 | 21 | 28 | 35 | 42 |
| At 20° C. | 0 | 0 | ± | ++ | +++ | ++++ |
| At 37° C. | 0 | 0± | + | +++ | ++++ | ++++ |

EXAMPLE 4

Several samples were prepared by the procedure described in Example 1 except that the sponges were molded with a 6 cm diameter and 2.5 cm depth without a central excavation. Each sponge had the characteristics shown below in Table V:

TABLE V

| | |
|---|---|
| Size - diameter of cylinder | 60 mm |
| - thickness | 25 mm |
| Dry weight (g) | 2.08 ± 0.05 |
| pH | 4.5 − 5.0 |
| Density ($mg/cm^3$) | 37.6 ± 2.0 |
| $T_s$ °C. | 75 ± 4 |
| Water binding capacity (a) (g $H_2O$/g) | 45 ± 5.0 |
| Rate of wetting (b) (g $H_2O$/g/10 sec) | 41 ± 3.0 |
| Resilience (c) (g) | 695 ± 20 |
| Rebound (d) (in % of original thickenss) | 97 ± 3 |

(a) Refers to total volume of water trapped and bound inside the sponge.
(b) Measured with prewetted sponge to simulate the in vivo situation.
(c) Refers to pressure in grams needed to compress wet sponge to 50% of original thickness.
(d) Refers to extension of sponge compressed as described under (d) 60 sec. after removing the load. Value is given in percent of original thickness of the sponge (2.5 cm).

Thirty volunteers having an average age of 27 years were provided with the above prepared collagen sponges. The sponges were moistened prior to use and the sponges were introduced either through self-administration or through application by a gynecologist; the sponges were placed in the upper vault of the vagina proximal to the cervix. The collagen sponges were left in place from a period of 2 days to 27 days between menstrual periods. No discomfort was reported by any of the users or any of their sexual partners. Of the 30 volunteers, 25 were classified as sexually active users, 3 of whom reported the incidence of odor occurring after a period of 3–4 days which was relieved by removal of the sponge, washing it in tap water, and reinserting it. Each of the volunteers were subjected to a gynecological examination subsequent to the use of the sponge; no incidence of vaginal irritation or infection was reported by the inspecting gynecologist. Average retention time was 7 to 9 days when taking into account the removal of the sponges for evaluation by gynecologists. Average retention time without the removal for evaluation would have been much higher.

EXAMPLE 5

Contraceptive sponges were prepared as described in Example 4. Three volunteers self-administered the sponges, after pre-moistening in tap water, and were inserted in the upper vault of the vagina proximal to the cervix. The sponges were inserted prior to intercourse and remained in situ for a period of from 2 to 8 hours after intercourse. The sponges were subsequently removed by gynecologists and a sperm penetration examination conducted in the cervical mucosa of each volunteer. No sperm penetration could be found.

EXAMPLE 6

Several sample sponges were prepared as set forth in Example 4, were pre-moistened in tap water, and were self-administered by three volunteers by insertion in the upper vault of the vagina proximal to the cervix. Coitus was simulated and orgasm induced in the volunteers through the utilization of an artificial penis within which was mounted a duodenoscope to permit continuous filming of the sponge during orgasm. The sponge was observed to continuously cover the cervix of the uterus and maintain intimate contact with the vaginal walls.

While the present invention has been described in the light of human use, it will be obvious to those skilled in the art that the process, the product and its use are applicable to those animals whose anatomical description includes reproductive organs equivalent to the human vaginal tract.

What is claimed is:

1. A contraceptive device for insertion in the upper vault of the vagina proximate the cervix comprising:
(a) a reconstituted collagen mass having a size and shape for insertion in the upper vault of the vagina;
(b) said collagen mass having a porous sponge structure with pore diameters ranging from 80u to 1400u.

2. The contraceptive device of claim 1 wherein the average pore diameter is 400u.

3. The contraceptive device of claim 1 where an extract of said collagen mass has a pH of from 4.0 to 6.5.

4. The contraceptive device of claim 1 wherein an extract of said collagen mass has a pH of from 4.5 to 6.0.

5. The contraceptive device of claim 1 wherein said collagen mass has a density of from 30 to 45 milligrams per cubic centimeter.

6. The contraceptive device of claim 1 wherein said collagen mass has a density of from 35 to 40 milligrams per cubic centimeter.

7. The contraceptive device of claim 1 wherein said collagen mass includes cellulose fibers in an amount equal to 5% to 15% of the dry weight of collagen in said mass.

8. The contraceptive device of claim 1 wherein said collagen mass includes cellulose fibers in an amount equal to approximately 10% of the dry weight of collagen in said mass.

9. The contraceptive device of claim 1 wherein said collagen mass includes viscose fibers in an amount equal to approximately 10% of the dry weight of collagen in said mass and wherein said viscose fibers have a length of from 0.5 to 2 centimeters and a diameter of from 50u to 150u.

10. The contraceptive device of claim 1 wherein said collagen mass includes an effective amount of a spermicidal agent.

11. The contraceptive device of claim 1 wherein said collagen mass includes an effective amount of zinc chloride as a spermicidal agent.

12. The contraceptive device of claim 1 wherein said collagen mass includes an effective amount of a bactericidal agent.

* * * * *